United States Patent
Goldberg et al.

(10) Patent No.: US 7,834,320 B2
(45) Date of Patent: Nov. 16, 2010

(54) REMOTE BIOLOGICAL, CHEMICAL AND EXPLOSIVE DETECTOR

(76) Inventors: Bar-Giora Goldberg, 3521 Mercer La., San Diego, CA (US) 92122; Gioia Messinger, 1897 Sienna Canyon Rd., Encinitas, CA (US) 92024

( * ) Notice: Subject to any disclaimer, the term of this patent is extended or adjusted under 35 U.S.C. 154(b) by 36 days.

(21) Appl. No.: 11/295,681

(22) Filed: Dec. 6, 2005

(65) Prior Publication Data
US 2006/0249683 A1 Nov. 9, 2006

Related U.S. Application Data

(60) Provisional application No. 60/633,032, filed on Dec. 6, 2004.

(51) Int. Cl.
*G01T 1/24* (2006.01)
*G01N 21/00* (2006.01)
*C12Q 1/68* (2006.01)

(52) U.S. Cl. .............................. 250/370.01; 250/338.5; 435/6

(58) Field of Classification Search ............ 250/370.01, 250/203.6, 214 R, 363.04, 326 C, 370.08, 250/559.22, 223 R, 338.5, 339, 341.8, 361 C, 250/370.02; 356/432, 328, 437, 438, 601, 356/73; 435/5, 287.2, 287.3, 287.4, 288.7, 435/6, 91.1, 91.2, 285.2, 287.1; 436/166, 436/167, 169, 172; 398/108, 109; 342/179; 343/721; 340/628, 632; 348/373
See application file for complete search history.

(56) References Cited

U.S. PATENT DOCUMENTS

| | | | | |
|---|---|---|---|---|
| 4,352,016 A | * | 9/1982 | Duffy et al. | 250/358.1 |
| 5,751,444 A | * | 5/1998 | Ward | 358/471 |
| 6,756,223 B2 | * | 6/2004 | Roberts et al. | 435/287.2 |
| 7,015,969 B2 | * | 3/2006 | Brown et al. | 348/373 |
| 7,057,743 B2 | * | 6/2006 | Merkel et al. | 356/601 |
| 7,075,645 B2 | * | 7/2006 | Gehrlein et al. | 356/328 |
| 2004/0191765 A1 | * | 9/2004 | Mozdy et al. | 435/5 |

* cited by examiner

*Primary Examiner*—Georgia Y Epps
*Assistant Examiner*—Don Williams (57) ABSTRACT

A distributed detector system is provided for remotely detecting agents indicating the presence of particular biological, explosive, or chemical targets. The distributed detector system may be used for security threat detection, manufacturing or environmental monitoring, or medical assaying. In the detection system, a central server or base station wirelessly communicates with a set of distributed detectors. In this way, the central server or base station is able to aggregate detection information, as well as apply additional processing and analysis to data collected at the detectors. Each detector has a reactive material, such as a silicon-polymer, that changes an optical property in the presence of a target agent. A camera is positioned to take images of the reactive material from time to time, and has local processing to determine when the reactive material has likely changed. In some cases, the detector may have sufficient processing power to classify the change according to its urgency or threat level. The detector wirelessly communications to the central server or base station, and appropriate alerts or notifications can be generated.

19 Claims, 6 Drawing Sheets

REMOTE BIOLOGICAL, CHEMICAL AND EXPLOSIVE DETECTOR

RELATED APPLICATIONS

This application claims priority to U.S. provisional patent application No. 60/633,032, filed Dec. 6, 2004, and entitled "Autonomous Remote Biological, Chemical, and Explosive Detector Using Color Imaging Analysis", which is incorporated herein in its entirety.

FIELD OF THE INVENTION

The field of the present invention is detection devices and methods. More particularly, a device and system is disclosed for remotely detecting biological, chemical, and explosive agents.

BACKGROUND

Since the events of Sep. 11, 2001, the world, and in particular the US, has become more aware of the need to monitor and detect terror, chemical, biological, and explosive threats. Typically, detection has either been a manual process, or has required a substantial installation process. For the manual process, people with detectors are positioned or rove in high risk areas to monitor for target threat agents. These agents are typically released or accompany known chemical, biological, or explosive threats. Each person monitors one or more manually-positioned detector, and reports when a threat is detected. However, such a manual detection process is highly intrusive, as it requires the presence of security and monitoring personnel at the risk site, and, it is not possible to fully protect a large area over extended periods due to staffing limitations. Also, some sensors may be checked only periodically as the security person makes their rounds. Since reaction time is critical in many threat situations, such a delay can have severe consequences.

The more permanently installed detection systems offer the benefit of being less noticeable in the risk area, but typically require the installation of a supporting power and data infrastructure to support a set of detectors. Also, since each detector is expensive, the overall cost of protecting an area is quite high, and limits the density of protection in all but the most critical areas. Unfortunately, in today's world, almost every building, event, and transportation system is a potential target of attack. With the cost and difficulty of installing these permanent systems, very few potential targets are actually being monitored. For example, it is generally agreed that security, especially security against biological, chemical, and explosive threats, needs to be improved for shipping and air cargo facilitates and containers, truck trailers, airport terminals, border check points, and other high value/high traffic locations. Also, the permanently installed systems are ineffective or uneconomical for temporary events. For example, an important dignitary may be making a one-hour speech at a hotel. Although the hotel may benefit from an installed detection system, it is not economically feasible to install a full threat detection system to support threat detection for just one speech. Therefore, such events are typically monitored by security personnel, which detracts from and interferes with the event. And, as described above, human monitoring may provide a threat response that is too slow to be effective.

Although terrorist threats are receiving much attention, other threats also need to be addressed. For example, manufacturing threats, such as gas leaks, biological agent release, and chemical spills pose a threat to workers as well as to the surrounding area. In another example, environmental threats, such as air pollution, water contamination, and the use of illegal pesticides and herbicides present vast areas that are currently difficult to monitor. In a final example, medical maladies and infections need to be identified prior to effective containment or treatment. Often, outbreaks occur in relatively remote areas, such as in rural areas of developing countries. Due to the cost of the medical assaying devices, and the sophistication needed to operate them, such devices are not readily available in these areas.

SUMMARY OF THE INVENTION

Briefly, the present invention provides a distributed detector system for remotely detecting agents indicating the presence of particular biological, explosive, or chemical targets. The distributed detector system may be used for security threat detection, manufacturing or environmental monitoring, or medical assaying. In the detection system, a central server or base station wirelessly communicates with a set of distributed detectors. In this way, the central server or base station is able to aggregate detection information, as well as apply additional processing and analysis to data collected at the detectors. Each detector has a reactive material, such as a silicon-polymer, that changes an optical property in the presence of a target agent. A camera is positioned to take images of the reactive material from time to time, and has local processing to determine when the reactive material has likely changed. In some cases, the detector may have sufficient processing power to classify the change according to its urgency or threat level. The detector wirelessly communicates to the central server or base station, and appropriate alerts or notifications can be generated.

In a more specific example, the distributed detector system is a security threat system for remotely detecting agents indicating the presence of particular biological, explosive, or chemical attacks. In the threat detection system, a central server or base station wirelessly communicates with a set of distributed threat detectors. In this way, the central server or base station is able to aggregate threat information, as well as apply additional processing and analysis to data collected at the detectors to further asses the threat. Each detector has a reactive material, such as a silicon-polymer, that changes an optical property in the presence of a target threat. A camera is positioned to take images of the reactive material from time to time, and has local processing to determine when the reactive material has likely changed. In some cases, the detector may have sufficient processing power to classify the change according to its threat level. The detector wirelessly communicates to the central server or base station, and appropriate alerts or warnings can be generated.

Advantageously, the detector system enables the deployment of a robust detection system that is minimally invasive on the local environment, does not require installing expensive data and power lines, but yet generates effective alerts as to the presence of biological, chemical, or explosive agents. The system may be quickly deployed and operational, and with the small size and low cost of the individual detectors, allows for dense detector presence in an area. Also, the detector may be configured to detect multiple agents, or may be readily fitted with a different reactive material when a different target agent is selected. The detection system may therefore be a highly effective monitoring system for public transportation systems, buildings, events, airports, or battle zone areas. The detection system may also be used in manufacturing, environmental, and medical applications. Since the

DETAILED DESCRIPTION OF THE PREFERRED EMBODIMENT

Figure 1:
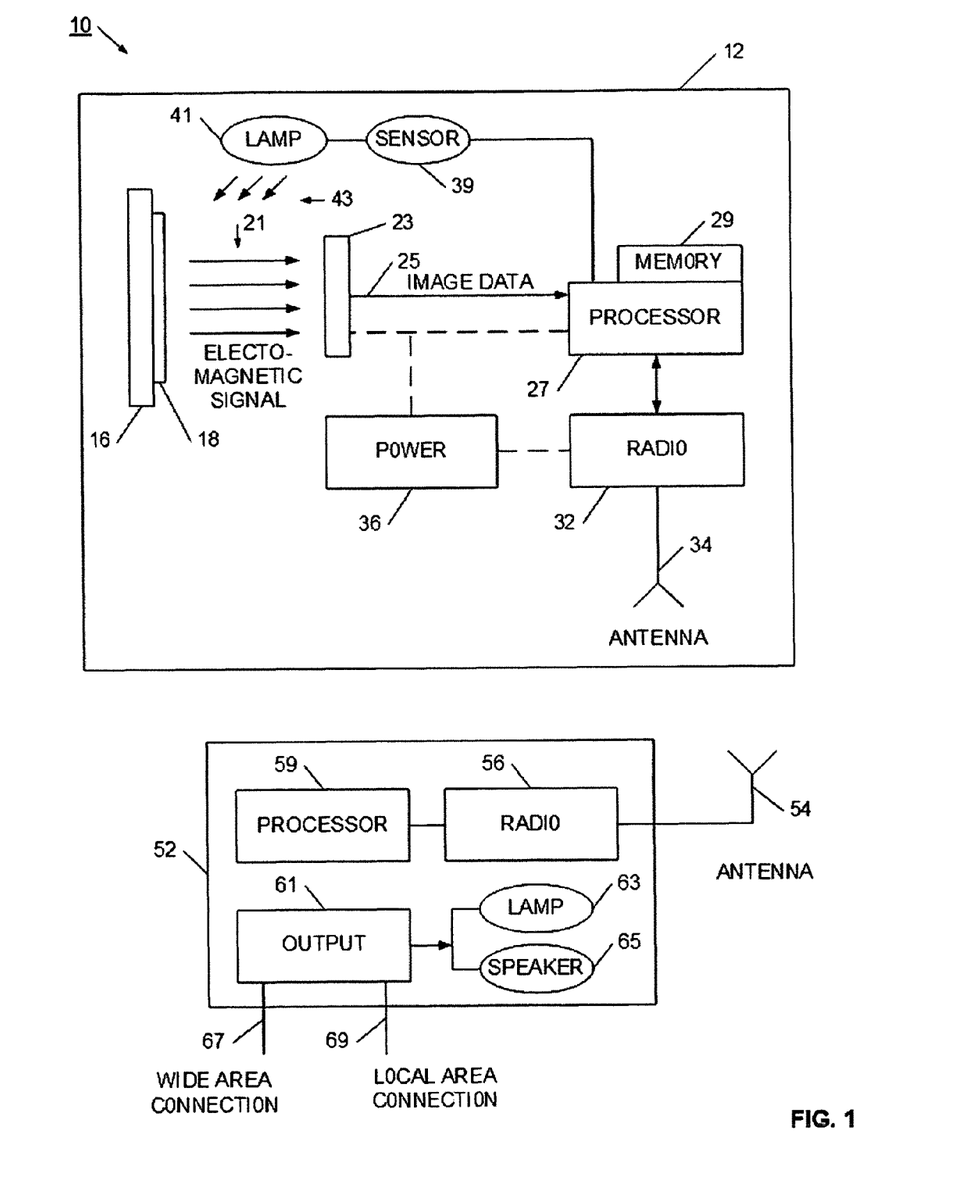
FIG. 1 is a block diagram of a detection system in accordance with the present invention.

Referring now to FIG. 1, an autonomous sensing system 10 is illustrated. Sensing system 10 enables a remote detector 12 to automatically and autonomously detect a target agent. For example, the detector 12 may be set to detect particular biological, chemical, explosive, or other target agents. When the target agent is detected, the detector 12 may send an alert to a base station 52. In this way, a remote detector is able to autonomously provide information regarding the presence of a target agent. Also, the detector 12 has sufficient intelligence and processing power to determine when the agent is present and to classify the threat or urgency the agent presents. For example, the detector may be set to detect the presence of a toxic gas. In the presence of the gas, the detector will be able to alert that the toxic gas is present, as well as classify its concentration to set the urgency or threat level. In this way, a much more urgent alert may be transmitted to the base station when a deadly level of the gas is detected. In a similar manner, a less urgent notification may be transmitted when the gas is detected in trace amounts.

The detector 12 has substrate 16 on which a reactive material 18 is positioned or disposed. The reactive material is selected to change an optically detectable characteristic in the presence of a target agent. In one example, the reactive material may be selected to change color in the presence of the target agent. In another example the reactive agent may change its reflective properties. A wide range of reactive materials exist for detecting biological, chemical, explosive, or infectious agents. In a specific example, the reactive material 18 is a silicon polymer material. Silicon polymer is well known for its ability to optically change in the presence of a target agent. Typically, a silicon polymer is selected for detecting the presence of one or more target agents. When the agent is present, the silicon polymer material typically changes color, and may change according to the concentration level or specific type of target agent. In a typical construction, a selected polymer is deposited onto a silicon wafer. In some cases, the silicon wafer may be used as a substrate 16, and in other cases a more substantial substrate may be used. In this regard, some polymers have a reversible detection mechanism, that is, the polymer returns to its normal state when the target agent is removed. Accordingly, the silicon polymer structure may be permanently or durably installed in the detector, which enables the use of a relatively insubstantial substrate, or even having the silicon itself act as a substrate. In other cases, the reactive material is destroyed upon detection of the target agent, so the reactive material must have a supporting substrate that allows for manufacture, storage, handling, and installation of the reactive material and its substrate. It will be appreciated that many materials may be used as supporting substrates.

The polymer sensors contemplated for use are materials (primarily Silicon wafers) with photoluminecent characteristics which change color in the presence of certain targeted analytes (explosives, gases, bio agents, volatile organic materials, etc. . . . ). These types of polymer sensors and nanostructures based on Silicon wafer technology have received a lot of attention in the last few years because of their sensitivity, reusability and low power consumption which makes them preferable for miniature remote sensing applications.

When light or other electromagnetic wave hits the reactive material 18, some of the wave is reflected back to an image sensor 22. The reflected wave 21 is reflected according to the optical properties of the reactive material, so this wave has information regarding the detection status of the reactive material. For example, the reflected wave may have color, density, or gradient information according to the reaction status of the reactive material. The reflected signal 21 is received by the imager 22. The imager 22 may be, for example, a CCD or CMOS sensor array. It will be appreciated that the sensor array may be selected and configured to more effectively detect the expected change in a reactive material. For example, if the reactive material is expected to make a change in a specific color range, the sensor may be optimized for operation in that expected color range. The design and use of CCD and CMOS sensors is well-known, so will not be discussed in detail.

Video imagers are comprised of an array of pixels which in and of themselves each is a photo detector. The pixels are then coated by color filters, Red, Green and Blue (RGB) to create a color imager. Most imagers have their color patterns arranged as squares with 4 elements—organized as RG/GB. The color green is repeated twice because green is the dominant color in our everyday world. This RG/GB arrangement is also called Bayer pattern. When exposed to light, the individual detectors collect their light intensity, in the color spectrum they are coated with, and the analog voltage they develop (proportional to light intensity) is then passed thru an on board ADC. This digital data is streamed out in a certain format, to create a file that represents the color image (in digital format).

The imager 22 generates image data 25, which may be in the form of a data stream or may be transferred as an image file. The image data may also represent all the image data from the imager, or less than all the data may be sent. For example, the sensor 22 may be configured to transfer only a window of data. This window may be static, or may be dynamically adjusted according to detector condition.

The image data 25 is received at processor 27. The processor 27 has a memory system 29 for storing data and application processes. The memory may include RAM, ROM, EPROM, or removable memory. In some cases, the memory system 29 may also include magnetic media, such as a hard disk drive. In this way, more data may be locally stored, which may be useful for historical analysis. Of course, it will be appreciated that memory system 29 may be selected to reduce power usage. In such a power reduced environment, the applicability of hard disks may be limited. The processor operates local processes for managing the image data, and for evaluating the presence of the target agent. For example, the processor may operate a principal component analysis (PCA) process on all or relevant portions of the image data. Principal component analysis is a classic and well known statistical method. In another example, the processor may operate pattern recognition or image recognition processes to evaluate the image data. Pattern recognition processes and image processing processes are well-known, so will not be discussed in detail. Image processing, pattern recognition and pattern classification software will be performed on the captured images locally (i.e. on-board the device) to enable good probability of detection and low false alarm rate. The image capture rate and the number of images to process to determine sufficient changes are to be determined.

The processor is able to use its local processes to evaluate the image data for the presence of a target agent. In more sophisticated detectors, the processor may also proceed to classify the threat. For example, the image data may be classified according to concentration level or which particular agents are present. Based on this classification, the processor will generate urgency or threat information according to the classification. The urgency or threat information may include all or part of the image data, processed image data, classification information, alert information, or other results from the processes performed on the image data.

The detector also has a radio 32 for transmitting the urgency or threat information to the base station 52. The radio 32 has at least a transmitter portion for wirelessly transmitting the urgency or threat information from antenna 34 to antenna 54 at the base station 52. Although antenna 34 is illustrated as being inside the housing of the detector, it will be appreciated that an external antenna may be used. The radio 32 may also have a receiver for receiving control commands from the base station. In this way, the base station may make status inquiries, request image data, or make configuration adjustments to the detector 12.

The radio may be a local area radio such as an ISM, 802.11, Bluetooth, or WiFi compliant radio. In another example, the radio is a wide area radio such as a wireless mobile device compliant with, for example, CDMA, GMS, GPRS, CDMA2000, WCDMA, PHS, or PCS. Also, the radio could be constructed to operate on a proprietary commercial or military standard. Additional processing may be done to compress, encrypt, or otherwise secure the transmission.

Figure 6:
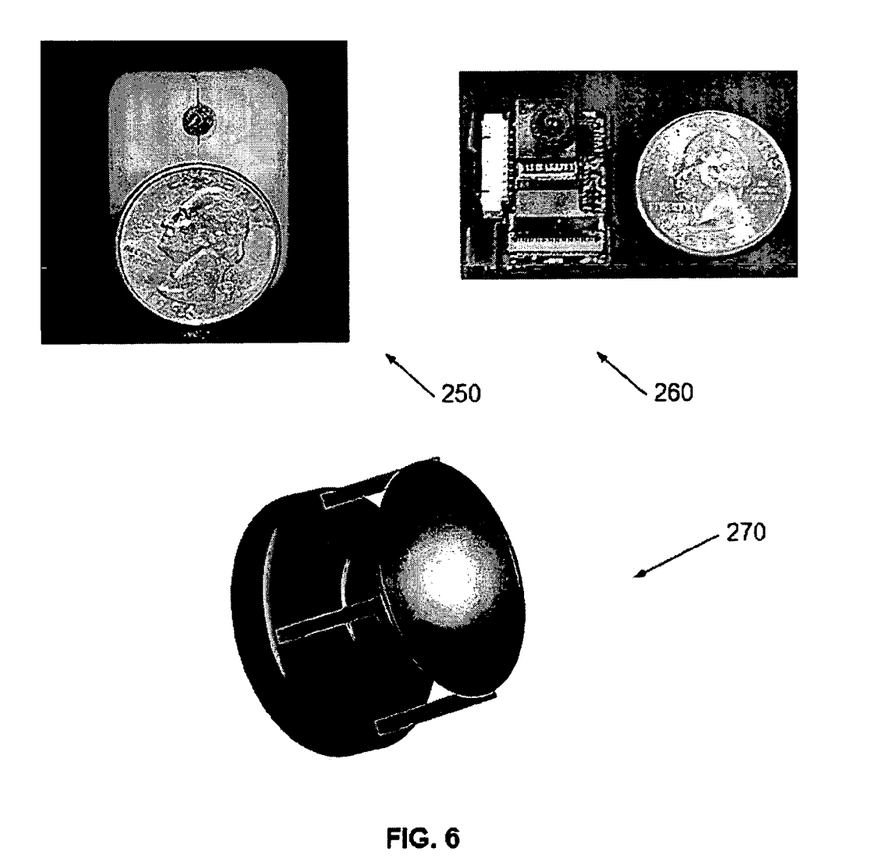
FIG. 6 has pictures of a camera/sensor/radio construction that may be used in the present invention.

In one particular example, the radio is similar to the radio used in the network sensor system as fully set out in co pending U.S. patent application Ser. No. 11/210,411, entitled "Network Sensor System and Protocol", filed Aug. 24, 2005, which is incorporated herein in its entirety. A picture of the radio/camera housing 250 is shown in FIG. 6, as well as the radio/camera printed circuit board 260. A reactive material may be positioned in front of the imager to allow the radio/camera system to capture images of the reaction material. Illustration 270 shows one structure for positioning a reactive material in front of the imager lens. This detector would be useful to transmit image data or processed information to a central hub in a power-restricted environment. The radio communicates to the hub with a wireless data link, and both the radio and the camera operate solely from a battery. Accordingly, the detector has no wire connections, so may be discreetly and simply installed. The detector may be operated in a power-saving sleep mode, and is minimally activated only for required periods of time. The detector may be activated responsive to a low power timer, or from another locally generated interrupt. The detector also implements power-saving transfer protocols to further reduce power needs.

Many detectors may be associated with a single central hub, and larger networked image systems may be arranged. It will be understood that other radio devices may be used.

The detector also has a source of power 36, which may be, for example, a battery or rechargeable battery. When more durable power is available, the power source 36 may be a DC or AC power supply. The power source 36 may also include solar, fuel-cell, or other sources of electrical power. Typically, the sensor acts responsive to reflected electromagnetic waves, so needs a light source to illuminate the reactive material. However, it will be appreciated that some reactive materials regenerate light or other electromagnetic signals due to the presence of a target agent, and therefore may not require an external source. In most cases, though, external illuminations needed, and ambient light may not always be available. Accordingly, an ambient light sensor 39 may be provided to detect when insufficient light is available. When insufficient light is available, a lamp 41 is illuminated to project light 43 on the reactive material 18. It will also be appreciated that the lamp may always be used to provide consistent and repeatable image data, even in changing ambient conditions. In one example, the lamp is a white LED, which provides a low-power optical illumination. It will also be appreciated that the lamp may be selected to assist in detecting the change in the reactive material. For example, if the change is expected to impact a particular frequency range, the lamp output may be selected to make the change more prominent. Although the discussion uses light as an example, it will be appreciated that visible light, infrared light, ultraviolet light, or other electromagnetic frequencies may be used.

The base station 52 has a radio 56 for receiving urgency or threat information from the detector 12, and also has a processor 59 for operating the base station as well as to provide additional processing capability. In some situations, the detector will operate in power restricted environments, so will be able to perform only limited detection and processing applications. The base station is likely to have access to more power and processing power, so is able to perform more complete real-time and historical analysis, urgency evaluation, or threat evaluation. In one arrangement, the detector is set to detect a change in the reaction material, and responsive to the detection, send image data to processor 59 for detailed processing. Processor 59 then proceeds to more fully evaluate the image data, and generates an alert, if appropriate. This configuration allows a relatively simple sensor, processor, and radio system to efficiently detect and gather urgency or threat information. This urgency or threat information is then aggregated at the base station or other server, and may be used to support automated or manual alerts, urgency analysis, or threat analysis.

The base station may include output 61, which could be, for example, an alert lamp or speaker. In this way, an alert can be visually or audibly generated at the base station. In another example, the output 61 includes a local area 69 or wide area 67 connection for sending alert information to another location. The alert may include image data, threat information, urgency information, or processed data. The connection may be wired or wireless, and may use public, commercial, government, or military communication systems.

The complete detection system may be generally described as follows: A miniature processing, imaging and communication platform is outfitted with silicon polymer sensor installed in front of the camera or on top of the imager. The imager captures images and uses an embedded processor to perform the image analysis looking for color or gradient changes which determine the presence of a target analyte. Detection of targeted agents at a certain level (determine by time, intensity or other variables) will trigger an alarm. To ensure that the detector operates in varied lighting conditions, the sensor platform will be equipped with white Light Emitting Diodes (LEDs) which will be activated when the imager senses marginal lighting condition.

The detector uses biological, chemical or explosive silicon (Si) polymer sensors, which change color in the presence of certain target analytes and be able to remotely detect and communicate these threats. At least two methods may be used to mate the color-changing detecting sensors and the color video imager: 1) coat very small pieces of the polymer sensors directly on the imager glass or 2) install a small piece of the polymer sensor on the focal point of a miniature camera. It will be appreciated that other methods and devices may be used. When the polymer sensor changes its colors in the presence of certain target analytes (be it chemical, biological or explosive) the imager along with imaging software will be used as a "spectral" analyzer. Color or shade gradient changes will be detected via signal processing algorithms (such as Principal Component Analysis (PCA) or other pattern and image recognition algorithms) that shall analyze color or luminescent changes, and alert users. Audible or graphic alerts can be used locally or these can be by transmitting wirelessly to a remote device or command post.

Advantageously, the detector system 10 enables the deployment of a robust detection system that is minimally evasive on the local environment, does not require installing expensive data and power lines, but yet generates effective alerts as to the presence of biological, chemical, or explosive agents. The system 10 may be quickly deployed and operational, and with the small size and low cost of the individual detectors, allows for dense detector presence in an area. Also, the detector may be configured to detect multiple agents, or may be readily fitted with a different reactive material when a different target agent is selected.

The detection system 10 may therefore be a highly effective security system for public transportation systems, buildings, events, airports, or battle zone areas. Since the detectors are small, autonomous, and noninvasive, they may be positioned for effective detection, and can operate unattended for long periods. Of course, the location and distribution of base stations will be selected according to the particular radio and radio coverage selected for the detector. The detection system may be advantageously used security threat detector to generate threat information, classify a threat, and generate alerts, such as biological, explosive, or chemical attack alerts. The detection system may also be used in manufacturing, environmental, or medical applications to generate urgency information, classify an urgent event, and generate alerts, such as biological, explosive, or chemical attack alerts. For example, the detection system may be used to monitor for a contaminant in a raw material for a manufacturing process. If the contaminant is detected by one of the distributed detectors, the detector may generate urgency information indicative of the contaminant, and if sufficient process power is available, proceed to classify the urgency, and generate appropriate alerts or notification. Such a distributed system may also monitor for leaks, spills, air quality, water quality, or other agents. In another example, the distributed system may monitor for production quality, ingredient purity, or process considerations. In this way, the distributed detection system is useful for monitoring production control in a manufacturing environment.

Further, the distributed nature of system 10 allows a system designer to adjust where processing occurs. This may be particularly useful, for example, when the detectors are used for assaying biological samples. Often, such analysis is process intensive, so is better suited to central processing. In this application, the remote detector uses local intelligence to determine when and what image data to capture, compacts and encrypts the image data, and sends the image data to a central location for analysis. This allows a relatively inexpensive and portable detector to be used at the site of biological interest, while benefiting from the powerful processing capability of the central server. The detector, then, operates as a rapidly deployable assaying device. More generally, the detection system enables a distributed spectrographic system.

In areas such as rapid optical immunoassaying for the detection of bioagents or to detect infectious agents in clinical specimens (i.e., Group A Strep, Group B Strep, *Chlamydia*, Influenza A and/or B, *Clostridium difficile*, etc.). The assay format utilizes specifically coated silicon wafers that give the desired optical properties (controlled manufacturing and quality control maintains the precise thickness of the applied layers to retain the golden appearance of the unreacted surface). Antibody specific to the target agent is applied to the wafer to form a surface capable of specifically capturing target antigen.

Figure 2:
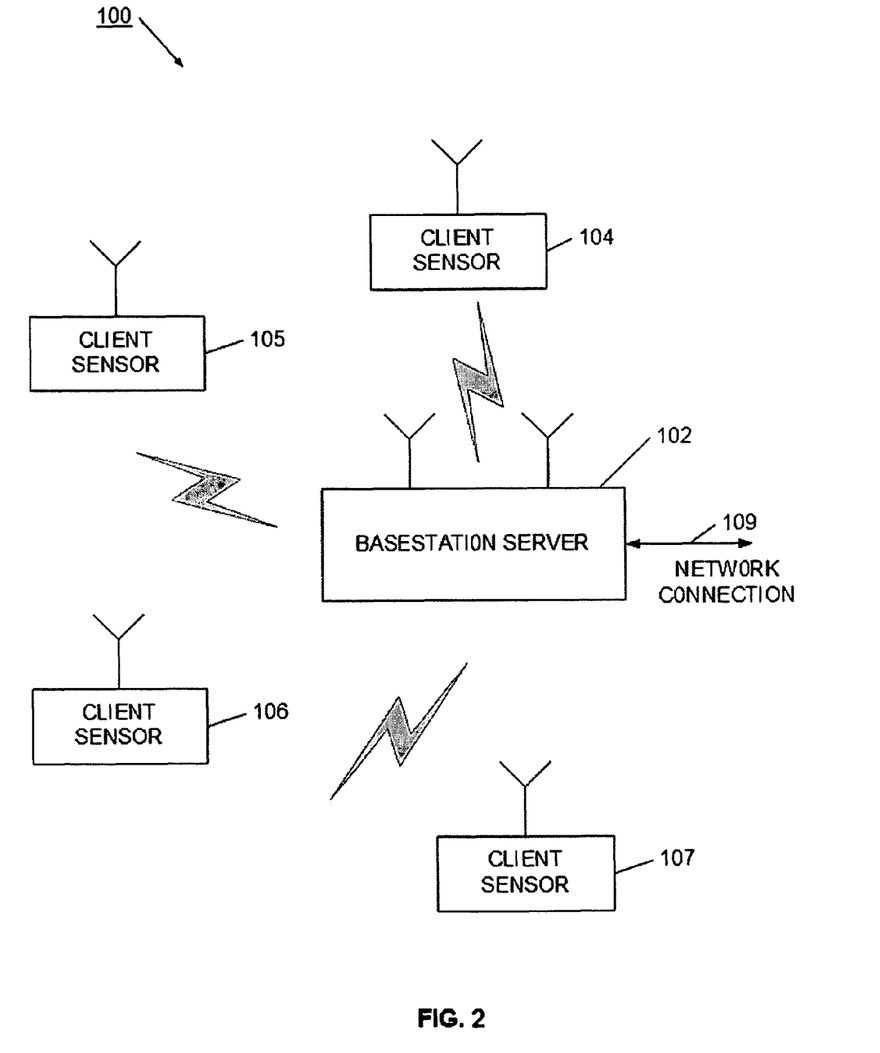
FIG. 2 is a block diagram of a distributed detection system in accordance with the present invention.

Referring now to FIG. 2, a remote detection system is illustrated. Remote system 100 has a set of detectors 104-107 that operate autonomously, but within radio range of base station server 102. Each detector is configured to monitor for one or more target agents. All of the detectors may be configured to detect the same target agent, or may be configured to test for different agents or sets of agents. In this way, a single detector network may share a network and central processing resources to detect a wide variety of threats.

In operation, the base station server 102 may transmit configuration, set up, or other commands to the client detectors 104-107. Also, the processor operating on each detector may be updated to reflect changes in the detection processes. For example, it may be discovered that the detectors are too often triggering with false alerts, so the detection algorithms may be changed to more precisely detect an alert. In another example, the detector may be set to check for a material reaction more or less often, depending on the general threat activity in an area. For example, a government office building may be only occasionally checked on the weekends, at shorter intervals during weekdays, and nearly continuously at a time when an important dignitary is visiting. By adjusting the rate of image capture and analysis, power may be preserved. It will be appreciated that system 100 may be used in a wide variety of environments, and in a wide variety of applications. By way of example, the detectors can be set to detect biological, chemical, explosive, medical, or fire indicating agents. Such a detection system may be highly desirable in security and military applications, as well as medical, environmental, and manufacturing applications.

Figure 3:
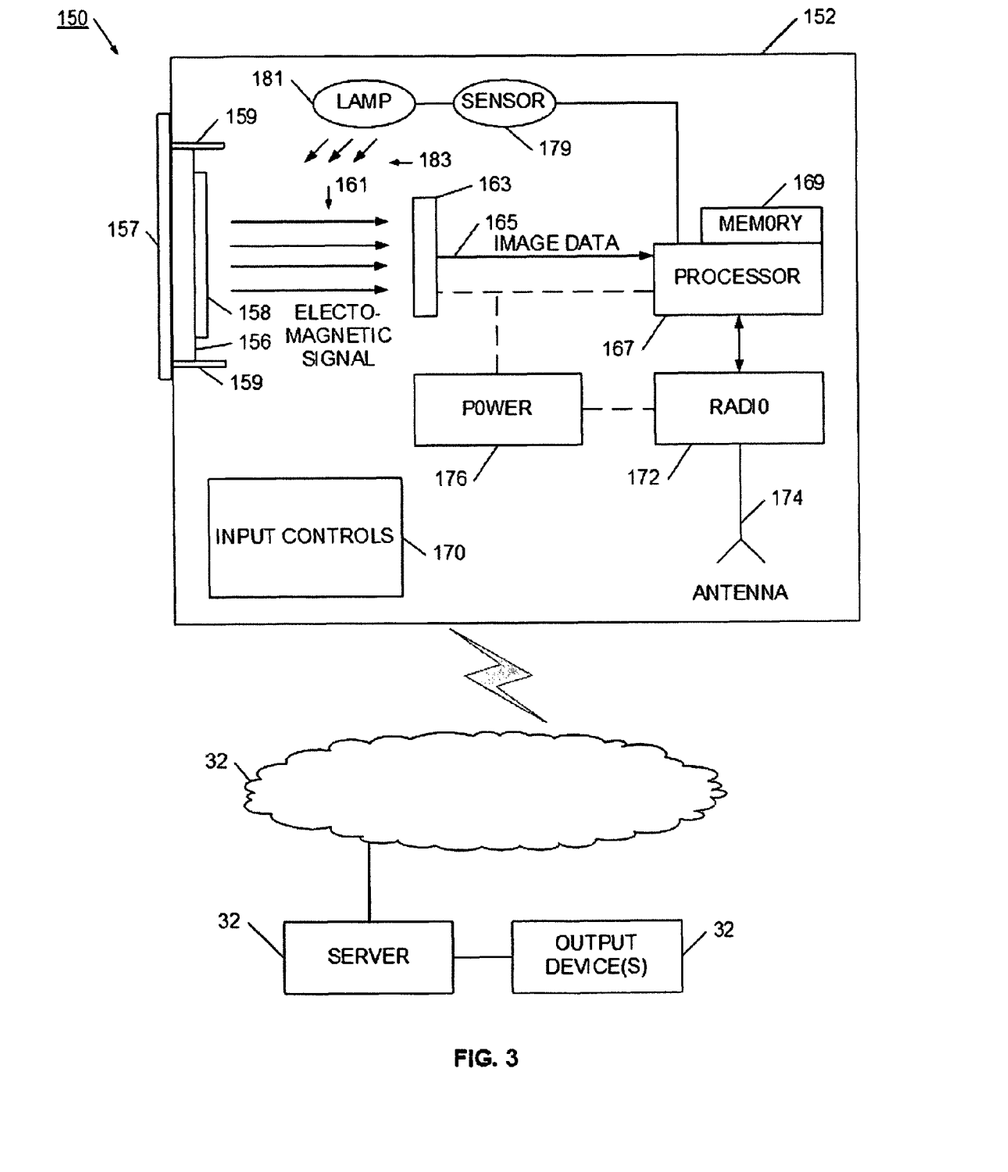
FIG. 3 is a block diagram of a distributed spectrographic system in accordance with the present invention.

Referring now to FIG. 3, a distributed spectrographic system is illustrated. The distributed spectrographic system 150 enables a remote detector 152 to automatically and autonomously perform a spectrographic process on a reactive target. For example, the spectrograph 152 may be set to process particular biological, chemical, explosive, or other target agents. When the detection process is complete, the spectrograph 152 may send spectrographic information or an alert to a central sever 192 using communication networks 190. In this way, a remote spectrograph is able to autonomously provide information regarding the spectrographic fingerprint for a target agent. Also, the spectrograph 152 has sufficient intelligence and processing power to analyze the image data to classify the threat or urgency the result presents.

The spectrograph 152 has substrate 156 on which a reactive target 158 is positioned. The reactive target has known spectrographic qualities, which may change when certain impurities, contaminants, chemicals, explosives, or other target material is present. In another example the reactive target may change its reflective properties. When light or other electromagnetic wave hits the reactive target 158, some of the wave is reflected back to an image sensor 162. The wave 161 may be reflected according to the optical properties of the reactive target, so has information regarding the spectrum status of the reactive target. For example, the wave 161 may have color, density, or gradient information according to the status of the reactive target. In other spectrographic process, the process creates its own optical or electromagnetic emissions, so the wave 161 is not reflected, but is emitted from the reactive target.

The reflected/emitted signal 161 is received by the imager 162. The imager 162 may be, for example, a CCD or CMOS sensor array. It will be appreciated that the sensor array may be selected and configured to more effectively detect the expected change in a reactive material. For example, the reactive material is expected to make a change in a specific color range, and then the sensor may be optimized for operation in that expected color range. The design and use of CCD and CMOS sensors is well-known, so will not be discussed in detail.

The imager 162 generates image data 165, which may be in the form of a data stream or may be transferred as an image file. The image data may also represent all the image data from the imager, or less than all the data may be sent. For example, the sensor 162 may be configured to transfer only a window of data. This window may be static, or may be dynamically adjusted according to detector condition.

The image dated 165 is received at processor 167. The processor 167 has a memory system 169 for storing data and application processes. The memory may include RAM, ROM, EPROM, or removable memory. In some cases, the memory system 169 may also include magnetic media, such as a hard disk drive. In this way, more data may be locally stored, which may be useful for historical analysis. Of course, it will be appreciated that memory system 169 may be selected to reduce power usage. In such a power reduced environment, the applicability of hard disks may be limited. The processor operates local processes for managing the image data, and for evaluating the presence of the target agent. For example, the processor may operate a principal component analysis (PCA) process on all or relevant portions of the image data. Principal component analysis is a classic and well known statistical method. In another example, the processor may operate pattern recognition or image recognition processes to evaluate the image data. Pattern recognition processes and image processing processes are also well-known, so will not be discussed in detail.

The processor is able to use its local processes to evaluate the image data to evaluate the composition or contamination of the target. In more sophisticated detectors, the processor may also proceed to classify a threat, if present. For example, the image data may be classified according to concentration level or which particular agents are present. Based on this classification, the processor will generate threat information according to the classification. The threat information may include all or part of the image data, processed image data, classification information, alert information, or other results from the processes performed on the image data.

The spectrograph also has a radio 172 for transmitting the threat information or spectrographic data to a central sever 192. The radio 172 has at least a transmitter portion for wirelessly transmitting the threat information from antenna 174 to a wireless receiver connected to network 190. Although antenna 174 is illustrated as being inside the housing of the detector, it will be appreciated that an external antenna may be used. The radio 172 may also have a receiver, for receiving control commands from the base station. In this way, the base station may make status inquiries, request image data, or make configuration adjustments to the detector 152.

The radio may be a local area radio such as an 802.11, Bluetooth, or WiFi compliant radio. In another example, the radio is a wide area radio such as a wireless mobile device compliant with, for example, CDMA, GMS, GPRS, CDMA2000, WCDMA, PHS, or PCS. Also, the radio could be constructed to operate on a proprietary commercial or military standard. Additional processing may be done to compress, encrypt, or otherwise secure the transmission. The detector also has a source of power 176, which may be, for example, a battery or rechargeable battery. When more durable power is available, the power source 176 may be a DC or AC power supply. The power source 36 may also include solar, fuel-cell, or other sources of electrical power.

Sometimes, the detector may need a light source to illuminate the reactive target. Alternatively, the source may irradiate the reactive agent to cause it to emit elector-magnetic radiation. However, it will be appreciated that some reactive targets regenerate light or other electromagnetic signals due to spectrographic processes, and therefore may not require an external source. for example, the spectrograph may have a heater, a burner, a chemical applicator, or other device for reacting the target. In the case where external illumination is needed, ambient light may not always be available. Accordingly, an ambient light sensor 179 may be provided to detect when insufficient light is available. When insufficient light is available, a lamp 181 is illuminated to project light 183 on the reactive material 158. It will also be appreciated that the lamp may always be used to provide consistence and repeatable image data, even in changing ambient conditions. It will also be appreciated that the lamp may be selected to assist in detecting the change in the target.

Remote spectrograph 152 is constructed to enable easy replacement of the reactive material. An access door 157 is placed in the housing to allow a user to remove an existing reactive material from holder supports 159, and insert a new reactive material. This enables replacement of exhaust and reactive material, or allows a different type of reactive material to be loaded in the spectrometer. In some cases, the reactive material may need to be heated or burned for the target reaction to occur, so spectrograph 152 will have heating elements, burners, vents, fans and other support devices as needed.

The spectrographic device 152 may also have a user input controls. In this way, an operator may configure the spectrographic device, load samples, and control the measurement. For example, a user may visually inspect a spectrographic process, and may manually control when image data is captured. In another example, the operator may wait to start the test until particular ambient conditions exist.

Figure 4:
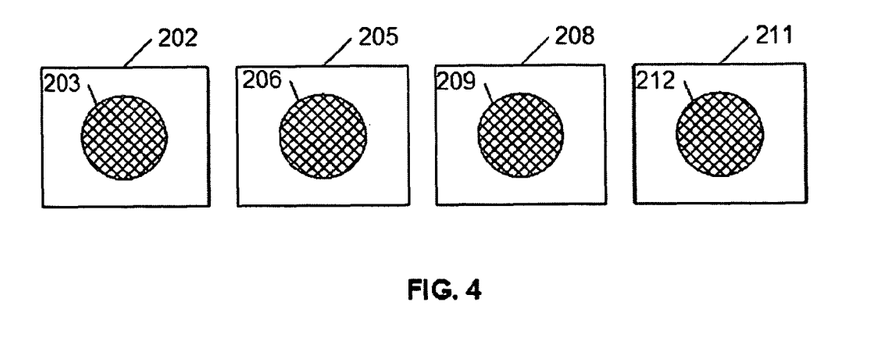
FIG. 4 diagrams of a set of substrates and reactive materials for use in a detector in accordance with the present invention.

Referring now to FIG. 4, a set of reactive materials is illustrated. Substrate 202 is a silicon wafer with a polymer 203 selected to detect a biological target such as anthrax, smallpox, or other bacterial or viral threat. Substrate 205 is a wafer with polymer 206 selected to detect a chemical target such as nerve gas, CO, or other toxic gas. Substrate 208 is a silicon wafer with a polymer 209 selected to detect an explosive such as TNT or RDX (plastic explosive). Substrate 211 is a plastic chip with a reagent disbursed on its surface to detect a blood component. It will be appreciated that other types of substrates and other types of reactive materials may be used.

Figure 5:
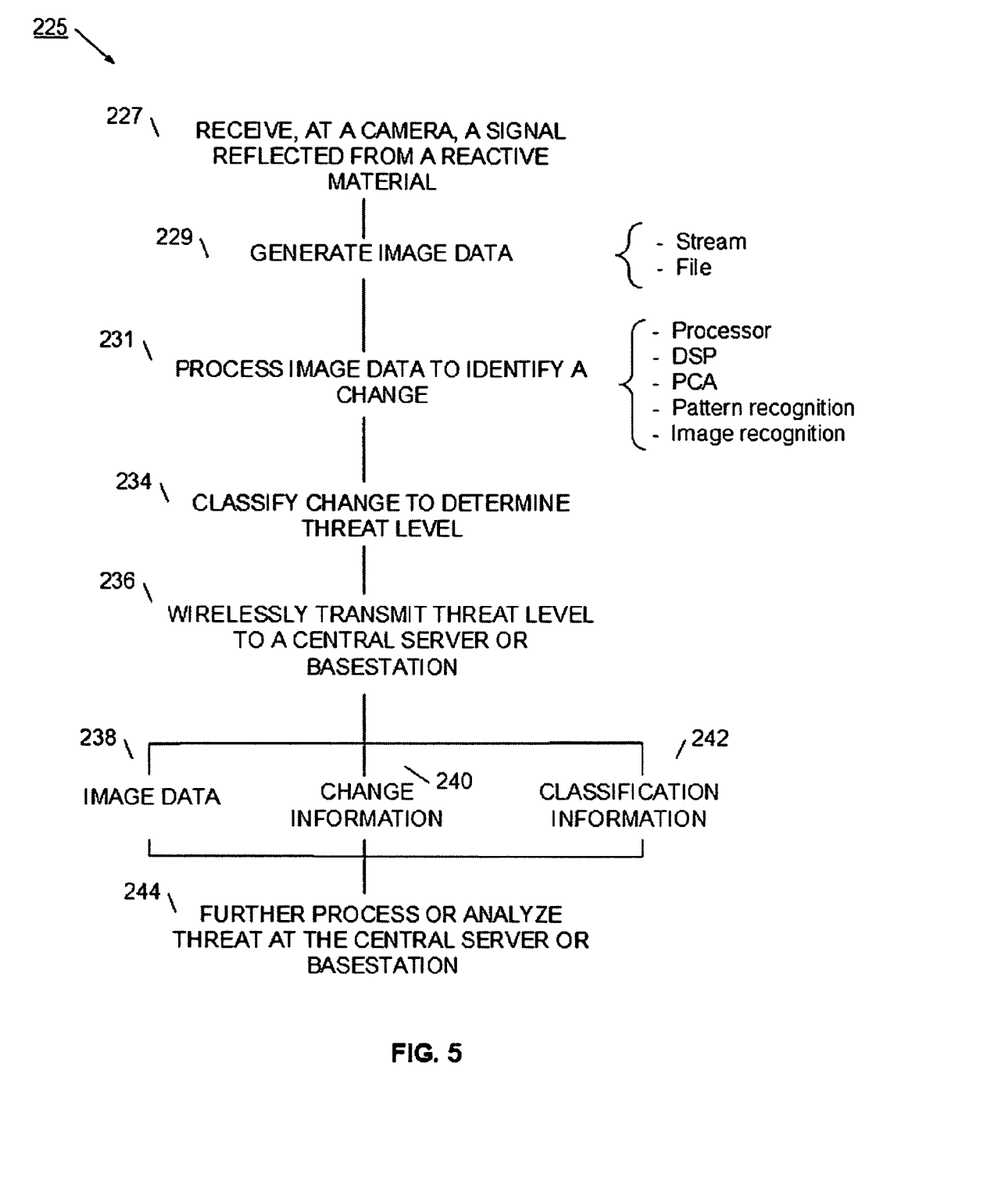
FIG. 5 is a flowchart of a process for collecting and classifying detector information in accordance with the present invention.

Referring now to FIG. 5, a method 225 for detecting a threat is illustrated. Method 225 operates in a detection system having a remote detector client that wirelessly communicates with a central server or base station. Such a distributed detection system may be readily deployed and activated to detect biological, explosive, chemical, fire, or other threat. Once operating, the detector captures images of a reactive material from time to time. The capture pace may be regular, irregular, or responsive to external commands or stimulus. It will be appreciated that capture rates will greatly impact power usage. As will be appreciated power consumption is a critical aspect of a battery-powered detector. Accordingly, capture rates may be set as slow as the application allows to conserve battery power. Once operating, the reactive material is illuminated, either by ambient light or by a lamp adjacent to the reactive material. The reflected wave is received at a camera as shown in block 227. The camera may be, for example, a CCD or CMOS imager. The imager generates image data as shown in block 229. The image data may be a data stream, or may be an image file. The data may also be for the whole active image array, or may be for a particular window of the array.

The image data is processed using a processor or digital signal processor (DSP) as shown in block 231. The image processing may include principal component analysis, pattern recognition, or image recognition. The complexity of the processing may be adjusted according to power availability and the level of processing required for accurate identification and classification of the agent. In some cases, a high level of processing may occur to determine and classify threats at the detector, while in other cases minimal processing is performed with the client, and additional processing is done at a central location. If appropriate, the detector processor classifies the change to determine a threat level as shown in block 234. Classification may be as simple as confirming a change occurred or that a particular change occurred, or may be much more sophisticated to determine types and levels of the target agent. Once the remote detector has determined a threat exists, threat information is wirelessly transmitted to a central server or base station as shown in block 236. The transmitted threat information may include image data 238, change information 240, or classification data 242. In some cases where transmission capability is limited, the detector clients will do most threat processing locally, and then transmit limited results or alert information back to the central server or base station. The base stations or server may do further processing to assess the threat as shown in block 249, including aggregating threat information from several centers. Also, the central server or base station may communicate raw or processed results to for example a central military or police command.

Figure 7:
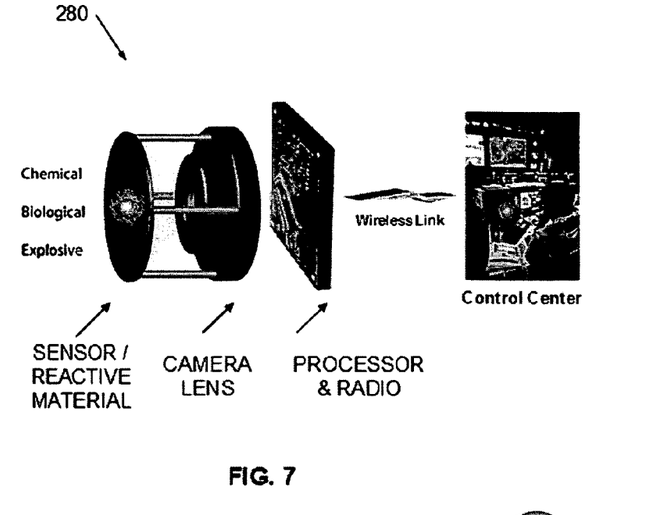
FIG. 7 is an illustration of a distributed detector system in accordance with the present invention.

Referring now to FIG. 7, a high-level system illustration is shown. System 280 has a sensor mounted in front of a camera imager so that the imager is able to capture high-resolution images of the sensor surface. A reactive material is on the sensor surface, which changes an optical characteristic in the presence of a target agent. Local processing is used to capture image data, as well as do at least an initial threat assessment. Data, results, and alerts may be communicated with a radio of a central processor or control center.

Figure 8:
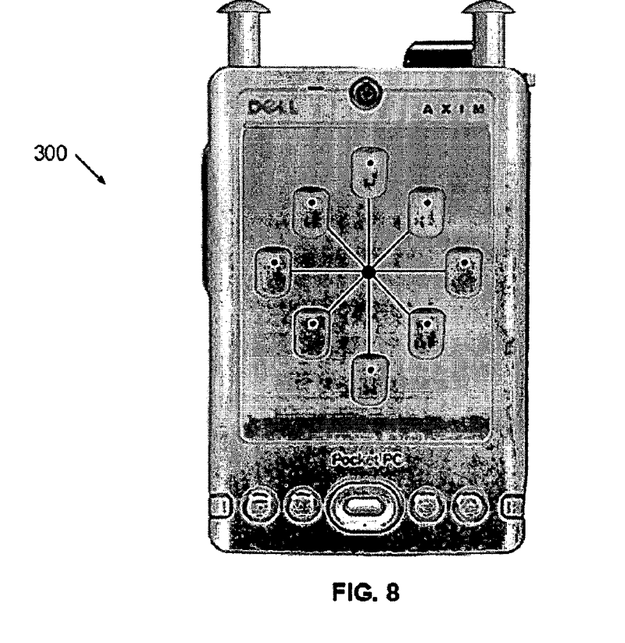
FIG. 8 is an illustration of a distributed detection system using a portable computing device as its central station.

Referring now to FIG. 8, a portable central base station 300 is illustrated. Base station 300 is constructed to receive wireless communication from a set of remote detectors, and to present aggregated threat information. Since base station 300 is can also portable and battery powered, a system using base station 300 can be rapidly deployed and activated without need for any wired infrastructure. Such a system would be highly desirable for setting up detectors at emergency sites, or for short term sporting or political events.

Chemical, Biological and Explosive detection using this system concept provides certain advantages over other types of detectors.
a. Small size and low cost
b. Excellent sensitivity
c. Excellent spatial resolution (pixel size is in the 2.7-5 um on side).
d. Autonomous operation and automated measurements
e. Automated adjustment of light conditions
f. Remote sensing over a considerable range
g. No moving parts
h. Multiuse sensors The detector system may be constructed using mostly off-the-shelf components. Imagers coupled with color changing Si sensors cooperate with embedded processors to create a very small and cost effective solution for the detection of target agents (biological, chemical or explosives). In addition, the detector allows for remote sensing and communications through the addition of a wireless communications transceiver on the sensing platform. The ability to image and process color changes with excellent spatial resolution with a CMOS imager demonstrates that this detector is not only functionally very attractive (can have a matrix of target agents on a single sensor, has superb sensitivity and is reusable) but that it also is practical and economical to implement.

While particular preferred and alternative embodiments of the present intention have been disclosed, it will be appreciated that many various modifications and extensions of the above described technology may be implemented using the teaching of this invention. All such modifications and extensions are intended to be included within the true spirit and scope of the appended claims.

What is claimed is:

1. A remote detector, comprising:
   a substrate member;
   a reactive material disposed on the substrate, the reactive material selected to change an optical property in the presence of a target agent;
   a camera positioned to receive electro-magnetic radiation from the reactive material and to generate image data that is indicative of the change in the optical property;
   a processor coupled to the camera and configure to receive the image data and generate a processed signal;
   a radio frequency (RF) transmitter coupled to the processor and configured to wirelessly transmit the processed signal to a base station; and
   a radio frequency (RF) receiver configured to receive remote commands from the base station.

2. The remote detector according to claim 1, further including a battery for powering the camera, processor, receiver, and transmitter.

3. The remote detector according to claim 1, wherein the reactive material is selected from the group consisting of: a biologically reactive material, a chemically reactive material, an explosive reactive material, and a medially reactive material.

4. The remote detector according to claim 1 wherein the reactive material is selected from the group comprising: color changing reagent, polymer, polymer coated silicon wafer, and photo-luminescent agent.

5. The remote detector according to claim 1, wherein the camera is a CCD device or a CMOS device.

6. The remote detector according to claim 1, further comprising:
   an imager substrate on the camera; and
   wherein the reactive material is disposed on the imager substrate.

7. A detecting system, comprising:
a remote sensor, further comprising:
  a substrate member;
  a reactive material disposed on the substrate, the reactive material selected to change an optical property in the presence of a target agent;
  a camera positioned to receive reflected electro-magnetic radiation from the reactive material and to generate image data that is indicative of the change in the optical property;
  a processor coupled to the camera and configure to receive the image data and generate a processed signal;
  a radio frequency (RF) transmitter coupled to the processor and configured to wirelessly transmit the processed signal to a base station;
  a radio frequency (RF) receiver configured to receive remote commands from the base station;
  a battery acting as a primary power source; and
the base station receiver further comprising:
  a radio frequency (RF) receiver configured to receive the processed signal; and
  an output device for providing a signal indicative of the processed signal.

8. The remote detecting system according to claim 7, further including;
  a radio frequency (RF) transmitter in the base station configured to transmit commands to the receiver in the remote sensor.

9. The remote detecting system according to claim 7, wherein the output device is selected from the group consisting of: a speaker, an audible alarm, an optical alarm, a lamp, a network connection, a local area transmitter, and a wide area transmitter.

10. The remote detecting system according to claim 7, wherein the base station is a portable handheld wireless device.

11. A method of generating an alert signal, comprising;
  receiving at a client camera device an electro-magnetic signal from a reactive material, the reactive material selected to change an optical property in the presence of a target agent;
  generating image data that is indicative of the change in the optical property;
  processing, using the client camera device, the image data to identify the change in the reactive material;
  classifying, using the client camera device, the change to determine presence of the target agen and to determine a threat or urgency level; and
  transmitting, using the client camera device, a radio frequency (RF) signal indicative of the target, threat or urgency information to a central server.

12. The method according to claim 11, wherein the receiving step includes receiving the electro-magnetic signal at a CCD sensor or a CMOS sensor.

13. The method according to claim 11, wherein the generating step includes generating an image data stream or an image data file.

14. The method according to claim 11, wherein the processing step includes using a DSP.

15. The method according to claim 11, wherein the processing step includes using a principal component analysis, pattern recognition, or image recognition process.

16. The method according to claim 11, further including classifying the threat or urgency as biological, infection, chemical, explosive, or fire.

17. The method according to claim 11, wherein the threat or urgency information includes at least some of the image data.

18. The method according to claim 11, wherein the threat or urgency information includes the processed image data or classification.

19. A portable spectrographic device, comprising:
  a material to be reacted, the reactive material selected to change an optical property in the presence of a target agent; and
  a housing constructed for hand-held portability and holding a remote sensor, the remote sensor comprising:
    a camera positioned to receive electro-magnetic radiation from the reacted material and to generate image data that is indicative of the change in the optical property;
    a processor coupled to the camera and configure to receive the image data and generate a processed signal;
    a radio frequency (RF) transmitter coupled to the processor and configured to wirelessly transmit the processed signal to a base station; and
    a radio frequency (RF) receiver configured to receive remote commands from the base station.

* * * * *